US006980292B2

(12) United States Patent
Sierakowski et al.

(10) Patent No.: US 6,980,292 B2
(45) Date of Patent: Dec. 27, 2005

(54) METHOD FOR THE PRODUCTION OF DYESTUFF PASTES

(75) Inventors: Claudia Sierakowski, Seeheim-Jugenheim (DE); Ines Mangels, Münster (DE); Zenon-Paul Czornij, Brighton, MI (US); Thomas Krüger, Eisingen (DE); Peter Hoffmann, Münster (DE); Thomas Frey, Mannheim (DE); Benno Sens, Neustadt/Weinstrasse (DE); Manfred Mielke, Heidelberg (DE); Paul Günthert, Schifferstadt (DE); Gerhard Berger, Stuttgart (DE); Peter Blaschka, Ludwigshafen (DE); Günter Etzrodt, Stuttgart (DE)

(73) Assignee: BASF Coatings AG, Munster (DE)

( * ) Notice: Subject to any disclaimer, the term of this patent is extended or adjusted under 35 U.S.C. 154(b) by 21 days.

(21) Appl. No.: 10/493,332

(22) PCT Filed: Nov. 22, 2002

(86) PCT No.: PCT/EP02/13139

§ 371 (c)(1),
(2), (4) Date: Jul. 14, 2004

(87) PCT Pub. No.: WO03/044109

PCT Pub. Date: May 30, 2003

(65) Prior Publication Data

US 2005/0002027 A1 Jan. 6, 2005

(30) Foreign Application Priority Data

Nov. 23, 2001 (DE) ................. 101 57 435

(51) Int. Cl.$^7$ .................. G01J 3/42; C09D 17/00
(52) U.S. Cl. ..................... 356/300; 356/402
(58) Field of Search ................. 356/300, 402

(56) References Cited

U.S. PATENT DOCUMENTS

| 5,022,758 A | 6/1991 | Schulz ............. 356/319 |
| 5,369,483 A | 11/1994 | Wilson ............. 356/300 |
| 5,953,129 A | 9/1999 | Anderlik et al. ..... 356/402 |
| 6,348,538 B1 * | 2/2002 | Buhl et al. ......... 524/513 |
| 6,535,283 B1 | 3/2003 | Heffels et al. ...... 356/300 |

FOREIGN PATENT DOCUMENTS

| DE | 19652791 | 7/1998 |
| WO | WO02/74866 | 9/2002 |

OTHER PUBLICATIONS

English Abstract for DE19652791 from EPO, Jul. 2, 1998.

\* cited by examiner

Primary Examiner—F. L. Evans

(57) ABSTRACT

The invention relates to a method of producing color pastes, in which a component comprising colorant particles is dispersed in a binder. In the method of the invention the dispersing operation is controlled by beaming excitational light of a defined wavelength range into a mixture of the component comprising colorant particles and the binder, detecting the light transmitted, reflected and/or scattered by the mixture and determining a sample spectrum, evaluating the sample spectrum and hence determining parameters of the color paste, and monitoring changes in the sample spectrum over time and terminating the dispersing operation when predetermined target parameters are attained.

11 Claims, No Drawings

METHOD FOR THE PRODUCTION OF DYESTUFF PASTES

CROSS REFERENCE TO RELATED APPLICATIONS

This application is a National Phase Application of Patent Application PCT/EP02/13139 filed on 22 Nov. 2002, which claims priority to DE 101 57 435.5, filed on 23 Nov. 2001.

DESCRIPTION

The present invention relates to a method of producing color pastes, in which a component comprising colorant particles is dispersed in a binder.

Color pastes, also called tinting concentrates, are a key constituent in the production of paints and coating materials. In order to be able to prepare a large number of different shades efficiently in the case of paints, for example, color pastes of a wide variety of pigments are stocked and are later mixed together with so-called letdown components to give the desired paint shade. The color pastes themselves are prepared by dispersing powder pigments into a binder adapted to the particular preparation task.

The colorant particles, such as powder pigments, for example, are manufactured industrially in a multistep batch operation. After the synthesis the pigments are obtained generally in a relatively coarsely crystalline form and are referred to as crude or coarse product. The crude product is usually dried to start with. The coarse crude pigments are reduced in size by an operation of activating/grinding. Smaller particles, stronger in color, are produced. Because of the broad particle size distribution resulting from the grinding, and because of the high propensity of the size-reduced particles to agglomerate, activating/grinding is normally followed by a treatment in organic solvents or water, in which the finely divided crude product, as is present after the coarser pigments have been ground, grows gradually under defined operating conditions to the size of a desired specification product with a narrower size distribution. This aftertreatment is also referred to as finishing. After the finish, the pigments are typically processed further in the form of a—preferably dried—presscake. In industrial pigment production it is usual to operate with constant finishing times. Owing to fluctuations in the feedstock and in the operating conditions, however, the coloristic properties of the finished pigments are subject to certain fluctuations. Generally, for example, after the end of the finishing operation, the desired hue angle, characteristic of the specification product, or the desired color strength is not attained. In that case attempts are made to achieve the desired coloristic properties by blending with another production batch. For example, one production batch with a color strength of 90% can be blended with another production batch with a color strength of 110% in order to achieve a lot having 100% color strength. Pigment product close to specification is therefore usually a mixture of pigments from different product batches.

The pigment lot, correctly blended in terms of the coloristic properties, is subsequently dispersed in a binder in order to produce the color paste. Dispersing apparatus used in paint preparation generally comprises stirred ballmills. In such mills the pigment particle agglomerates are broken up by mechanical interactions with the grinding beads, which are stirred by motor, and the pigments themselves are reduced in size, wetted, and homogenized. The dispersing operation is normally terminated after a predetermined duration or after a defined energy input has been reached, and the quality of the end product is examined.

Since the human eye is able to perceive even very small differences in color in coatings, paints or printing inks, quality control in the industrial production of such color pastes is of particular importance in order to achieve maximum reproduction of a defined color series and to guarantee consistent quality of the product. Normally, for this purpose, samples are taken of the color paste and are analyzed by means of conventional calorimetric techniques. To determine the color strength, for example, a portion of the color paste is blended with a portion of a white paste (test white) and subjected to measurement in a conventional calorimeter. Techniques of this kind are not only inconvenient but are also associated by diverse measurement errors, such as weighing errors, errors when mixing the components, and so on. German patent application DE 196 52 791 describes an improved measurement technique which allows direct determination of the color strength of a color paste and which therefore avoids the weighing errors mentioned above. It involves beaming excitational light in the infrared spectral range into a sample, and subjecting the light scattered back from the sample to spectral analysis, and correlating it with the color strength. According to DE 196 52 791 the beaming-in of light in the near infrared wavelength range is preferred since in this range the visible color of the color paste plays no part and the scattering intensity essentially represents a measure of the distribution of the particle size.

With the known technique, however, the ready-produced color paste is always subjected to a quality control examination. In order to prevent off-specification lots, therefore, the coloristic properties of the pigment lot used must lie within very narrow tolerances if, after an empirically determined, given dispersing time a color paste having the desired properties is to be produced. The requirements imposed on the pigment manufacturer are therefore stringent, and this translates to a correspondingly inconvenient and expensive production process.

It is an object of the present invention, then, to provide a method of producing color pastes by dispersing a component comprising colorant particles in a binder, in which the coloristic properties of the component comprising the colorant particles can have a relatively broad fluctuation without the properties of the resulting color paste being impaired.

This object is achieved through the method according to present claim 1.

In accordance with the invention the dispersing of the colorant particles into the binder is monitored instrumentally, and in particular the coloristic properties of the color paste is determined continuously or at regular intervals during the dispersing operation. The invention accordingly provides a method of producing color pastes, in which a component comprising colorant particles, pigment particles for example, is dispersed in a binder, the method being characterized in that the dispersing operation is controlled by beaming excitational light of a defined wavelength range into a mixture of the component comprising the colorant particles and the binder and detecting the light transmitted, reflected and/or scattered by the mixture. The detected light is broken down spectrally in order to determine a sample spectrum. The sample spectrum may then be, for example, a transmission or absorption spectrum or a reflectance spectrum. Sample spectra can also be obtained by means of attenuated total reflection. By using different probes it is possible to use two or more spectral detection methods at the same time: for example, the attenuated total reflection together with the reflectance. From each individual sample spectrum it is possible to determine characteristic parameters and in particular, with conventional calorimetric methods, the coloristic properties of the color paste. In accordance with the invention, changes in the sample spectrum or sample spectra and/or in the color paste parameters determined therefrom are monitored over time. The dispersing operation is finally terminated when a predetermined spectrum or predetermined target parameters are attained.

In contrast to the conventional production operation for color pastes it is possible for the coloristic properties of the colorant particles employed to exhibit a relatively broad fluctuation, since a predetermined dispersing time is not operated. The dispersing time is instead adapted to the result that is to be achieved. In this context the invention exploits the fact that associated with increasing dispersing time there is a reduction in the size of the agglomerates formed by the colorant particles or, in the case of larger particles, in the colorant particles themselves, and that the particle size in turn influences the sample spectrum and the parameters resulting therefrom. Thus, in the case of pigments and dye particles a change in the particle size or particle size distribution is associated with a change in the color properties themselves, which may be manifested, for example, in a change in the tristimulus values X, Y, Z (definition according to DIN 5033, Sheet 3). Depending on the dispersing method chosen, it is also possible to vary other factors which affect the particle size, besides the dispersing time. For example, when using a ballmill, the speed of the rotor can be altered.

Colorimetric parameters of this kind can be based, for example, on the CIELAB color system and may include one or more of the following variables: hue, chroma, lightness, color difference ($\Delta E$). There are commercially available programs (for example, the colorimetry program in the Aspect software from Carl Zeiss, Oberkochen) which can be used to convert measured reflectance values, for example, directly into CIELAB color coordinates. In this way it is possible, for example, to follow the color locus of the paste over time during the dispersing operation.

Other suitable parameters may be, for example, the value of the sample spectrum at a defined wavelength, or a combination of two or more values at different wavelengths.

If the sample spectrum is evaluated directly, then in many cases no direct connection will be known between the desired product properties and the measured spectra. In this case it is possible to determine the connection between sample spectrum and coloristic product properties by means of correlation techniques as well. This can be done, for example, using chemometric methods, i.e., statistical correlation techniques in which an initially high-dimensional data volume is reduced to a smaller dimensional number by means of linear or nonlinear analysis of principal components. Statistical evaluations such as regression analyses or cluster analyses can then be applied to these data. With the aid of artificial neural networks it is also possible for there to be an adaptive fitting to an algorithm, which correlates the product properties with the measured reflectance spectra.

Corresponding evaluation techniques are known. For instance, besides the abovementioned DE 196 52 791, reference may also be made to DE 196 26 785 A1, in which a process is described for the continuous color measurement of polymeric molding compounds, where a scattered-light sensor is mounted in the head of an extruder. By evaluating reflectance spectra, which are compared with a standard, it is possible to determine dye concentrations in a polymer melt. A method of determining dye concentrations in polymer melts is also described in U.S. Pat. No. 5,369,483, again based on the evaluation of scattered light measurements.

U.S. Pat. No. 5,369,483, moreover, mentions that color coordinates can be derived from the scattered-light spectra obtained.

The method of the invention therefore makes it possible to produce color pastes at more favorable cost, since the colorant particles used are required to satisfy less stringent quality requirements.

Surprisingly it has further been found that the method of the invention not only allows a greater breadth of fluctuation of the coloristic properties of the colorant particles employed, but that instead of the mixture of colorant particles from different production batches that is normally used it is possible to disperse just a precursor from colorant particle production into the binder. The material in question here generally comprises relatively large particles or agglomerates, which through choice of a suitable dispersing time or a suitable energy input can be reduced to the size that is required for the desired colorimetric parameters of the color paste. With the method of the invention, therefore, it is possible to shorten the overall production operation on the part of the pigment manufacturers, thereby further reducing the overall costs of color paste production.

A "precursor" in the present context comprehends any particulate intermediate obtained between the synthesis of the colorant and the mixing of different production batches of the finished colorant particles. In accordance with a first version of the method of the invention the precursor comprises agglomerates of finely divided colorant particles. These can be, for example, agglomerates of finished pigments. The average particle diameter of the agglomerates prior to dispersing is more than 1 $\mu$m, preferably more than 10 $\mu$m. The average particle diameter is given by the average diameter of the volume distribution (definition according to DIN 53206, Sheet 1) with the method of light diffraction, for example. For this purpose there are commercially available instruments (for example, from Sympatec, Clausthal-Zellerfeld). With the method of the invention, then, it is possible to omit the last stage in pigment production, i.e., the mixing of different production batches for the fine tuning of predetermined calorimetric parameters. The agglomerates may also consist of finely divided pigment powder which has not yet been finished, such as is obtained after the activation/grinding of the crude pigment or coarse pigment.

In accordance with another version of the method of the invention the use is even envisaged of crude pigment or coarse pigment having an average particle diameter of more than 1 $\mu$m, preferably more than 10 $\mu$m, for dispersion into the binder. In that case, in the course of the dispersing operation, the crude pigment is reduced in size at the same time, preferably to an average particle diameter of less than 500 nm. With the method of the invention, accordingly, it is possible to use pigments in the form in which they are obtained immediately after synthesis for dispersion into the binder. Grinding and finishing of the crude pigment by the pigment manufacturer is no longer necessary. The size reduction of the pigments in the dispersing operation to below 500 nm can be demonstrated, for example, by measuring the particle size by the method of photon correlation spectroscopy. From this, the average diameter is obtained as the average diameter of the volume distribution. Corresponding instruments are available from Malvern, Herrenberg, among others.

It is preferred to determine the sample spectrum in a wavelength range between 175 and 3000 nm, more preferably between 200 and 1000 nm. It is advantageous to beam in excitational light having a very uniform intensity distribution in the chosen spectral range. Advantageously, however, the spectrum of the light source itself will also be recorded, and the measured sample spectrum weighted accordingly.

In the ongoing dispersing operation it is possible to take samples at regular intervals and subject them to spectroscopic analysis in order to investigate the instantaneous properties of the color paste. Under usual industrial dispersing conditions, sampling at intervals of 5 to 15 minutes is generally sufficient to allow the dispersing operation to be monitored with the required accuracy.

With particular preference, however, the mixture of the component comprising the colorant particles and the binder is subjected to inline spectroscopic analysis in the ongoing dispersing operation. For this purpose it is possible to use fiber-optic probes, examples being back scattering, transmission, reflectance or ATR (attenuated total reflection) probes, as described by Heffels et al. in *Part. Part. Syst. Charact.* 15 (1998) 211–218. A new kind of ATR probe is also described in the applicant's German patent 198 56 591 C2. With particular advantage the fiber optics are arranged in an immersion probe having at its front end an optically transparent measuring window. The immersion probe is typically configured as an elongated probe which can be fastened, for example, by a flange connection in the lid of a stirred tank, and immersed into the medium present in the tank. For dispersing operations the probe is advantageously mounted in a conveying line between a circulating pump and the dispersing apparatus, a stirred ballmill for example.

Particularly suitable for investigating color pastes are reflectance probes and ATR probes, since with this arrangement of sensors the light is not required to penetrate deep into the surrounding area. In the case of reflectance probes, the typical depth of penetration of the irradiated light is in the region of a few micrometers, and in the case of ATR probes in the region of a few wavelengths of the irradiated light. The front end of the probe would advantageously be designed to be as smooth and flat as possible, thereby ensuring effective exchange of the medium in the direct boundary layer to the transparent window. With particular advantage the conveying line is narrowed in the region of the probe in order to prevent, or to remove, deposits on the probe window, by means of the venturi effect which occurs.

In the method of the invention it is possible to employ a very wide variety of particulate colorants, such as phthalocyanines (e.g., P.B. 15; P.G. 7; P.G. 36), isoindolines (e.g., P.Y. 109, 110, 139; P.O. 69; P.R. 260), perylenes (e.g., P.R. 123, 149, 178, 179, 190, 224; P.V. 29), and also anthraquinonoide species (for instance, indanthrones (e.g., P.B. 60), flavanthrones (e.g., P.Y. 24), bismuth vanadate (e.g., P.Y. 184), iron oxides (e.g., P.R. 101), $TiO_2$ mixed oxides (e.g., P.Y. 53, P.BR. 24), lead chromates (e.g., P.Y. 34, P.R. 104) and pyranthrones (e.g., P.O. 40, 51; P.R. 216, 226)), for example.

The invention is illustrated below with reference to two working examples.

In the examples the dispersing operation is monitored by means of an inline reflectance probe at intervals of 10 minutes by measuring the reflectance spectrum in the wavelength range from 200 nm to 1000 nm. To this end, the window at the tip of the rod-shaped reflectance probe is immersed in a pumpline between a conveying pump and a ballmill, which is used for dispersing. At this point the channel is narrowed in order to prevent possible deposits on the probe window due to the venturi effect which occurs here.

EXAMPLE 1

Production of a Color Paste Using a Finished Precursor

From the pigment production operation, finished presscake (P.G. 15, average particle size<200 nm) is taken.

A 1000 ml reservoir vessel is charged with 240 g of a 50% strength binder solution (acrylate-modified aqueous polyurethane dispersion). Using a dissolver disc, the binder solution is slowly stirred. 250 g of the 40% presscake are added and the mixture is homogenized using a dissolver. The rotational speed is raised to 20 m/sec. and the millbase is treated with the dissolver for 20 minutes so as to predisperse very coarse agglomerates.

The millbase is subsequently introduced into the stirred ballmill and the particles are distributed in the medium by means of grinding media. The peripheral speed of the mill rotor is 6–16 m per second. The end of dispersing is reached when the average size of the agglomerates has reached less than 500 nm and when the color strength level has approximately doubled.

The dispersing operation is monitored as set out above.

The condition for terminating the dispersing operation is when the absorption determined from the last reflectance spectrum measured, at a particular wavelength, remains constant in comparison to preceding spectra and the hue has reached a predetermined value.

EXAMPLE 2

Production of a Color Paste Using Nonactivated Crude Product

From operation, dried crude product perylene (P.R. 179, average particle size>5 $\mu$m) is taken.

A 1000 ml reservoir vessel is charged with 400 g of a 30% strength binder solution (acrylate-modified aqueous polyurethane dispersion). Using a dissolver disc, the binder solution is stirred slowly. 100 g of the dried crude product, with a coarseness of up to 5 $\mu$m, are added, and the viscosity of the mixture rises. The rotational speed is raised to 20 m/sec. and the millbase is treated with the dissolver for 20 minutes, so that very coarse particles are predispersed.

Subsequently the millbase is introduced into a stirred ballmill and the particles are reduced in size using grinding media.

The dispersing and size reduction operation is again monitored as set out above.

The end of the dispersing operation has been reached when the average particle size has dropped to below 500 nm and when the color strength level of the paste produced by a conventional route has been reached approximately. The condition for termination is when the absorption determined from the last measured reflectance spectrum at 450 nm remains constant in comparison to preceding spectra and when the hue has reached a value of below 26°.

What is claimed is:

1. A method of producing color pastes comprising dispersing a component comprising colorant particles in a binder, wherein the dispersing is controlled by a process comprising beaming excitational light of a selected wavelength range into a mixture of the component comprising the colorant particles and the binder, detecting the light transmitted, reflected, and/or scattered by the mixture, determining a sample spectrum, evaluating the sample spectrum and determining parameters of the color paste, and monitoring changes in the sample spectrum over time and terminating the dispersing when predetermined target parameters are attained.

2. The method of claim 1, wherein the component comprising colorant particles is a precursor for a pigment production process, and while the component is dispersed into the binder, it is reduced in size during dispersing.

3. The method of claim 2, wherein the precursor comprises agglomerates of finely divided pigments, and the agglomerates have an average particle diameter of more than 1 μm.

4. The method of claim 3, wherein the agglomerates comprise finished pigments.

5. The method of claim 3, wherein the agglomerates comprise nonfinished ground pigments.

6. The method of claim 2, wherein the precursor comprises crude pigment or coarse pigment having an average particle diameter of more than 1 μm.

7. The method of claim 1, wherein the sample spectrum is determined in a wavelength range between 175 and 3000 nm.

8. The method of claim 7, wherein chemometric methods are used to determine one or more parameters of the color paste.

9. The method of claim 1, wherein the mixture of the component comprising colorant particles and the binder is obtained by regular sampling in the ongoing dispersing and the samples are subjected to spectroscopic analysis.

10. The method of claim 1, wherein the mixture of the component comprising colorant particles and the binder is subjected to inline spectroscopic analysis in the ongoing dispersing.

11. The method of claim 10, wherein at least one fiber-optic probe is used for the spectroscopic analysis of the mixture.

* * * * *